United States Patent
Cross et al.

[11] 3,932,639
[45] Jan. 13, 1976

[54] 2 AND 3-SUBSTITUTED-4-(HETEROCYCLIC-AMINO-SULFONYL)BENZENE SULFONAMIDES AS CEREBRAL VASODILATORS

[75] Inventors: Peter Edward Cross; Brian Gadsby, both of Canterbury, England

[73] Assignee: Pfizer Inc., New York, N.Y.

[22] Filed: Oct. 4, 1974

[21] Appl. No.: 512,007

Related U.S. Application Data

[62] Division of Ser. No. 386,854, Aug. 9, 1973, Pat. No. 3,867,390.

[30] Foreign Application Priority Data

Aug. 12, 1972 United Kingdom............... 33720/72

[52] U.S. Cl. ............... 424/248; 424/244; 424/246; 424/275
[51] Int. Cl.² ............... A61K 31/535; A61K 31/33; A61K 31/54; A61K 31/38
[58] Field of Search ............ 424/248, 244, 246, 275

[56] References Cited
UNITED STATES PATENTS
3,165,550 1/1965 Holland et al. ...................... 424/321

FOREIGN PATENTS OR APPLICATIONS
2,340,010 5/1974 Germany

*Primary Examiner*—Donald B. Moyer
*Attorney, Agent, or Firm*—Connolly and Hutz

[57] ABSTRACT
Compounds of the formulae:

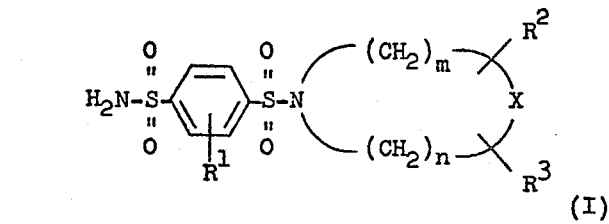

(I)

and

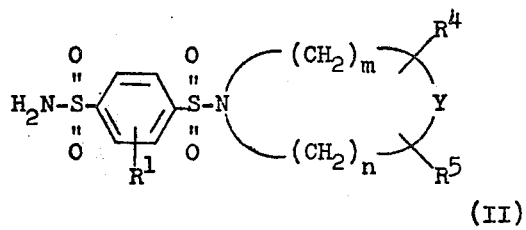

(II)

and the salts thereof with pharmaceutically acceptable cations wherein $R^1$ is 3-trifluoromethyl, chloro, bromo or fluoro; n and m are each two or three; X is oxygen or sulphur; $R^2$ and $R^3$, when taken separately, are each hydrogen or alkyl having 1 to 4 carbon atoms; $R^2$ and $R^3$, when taken together, are alkylene having 2 to 4 carbon atoms; Y is methylene or a single bond; $R^4$ and $R^5$, when taken separately, are each hydrogen, hydroxy or alkoxy having 1 to 4 carbon atoms, and $R^4$ and $R^5$, when taken together, are oxo or alkylene dioxy having 2 to 4 carbon atoms, each oxygen atom in $R^4$ and $R^5$, when taken separately, and in $R^4$ and $R^5$, when taken together, being separated from the nitrogen atom of the heterocyclic ring by two or more carbon atoms, said compounds being cerebral vasodilators.

5 Claims, No Drawings

2 AND 3-SUBSTITUTED-4-(HETEROCYCLIC-AMINO-SULFONYL)BENZENE SULFONAMIDES AS CEREBRAL VASODILATORS

CROSS-REFERENCE TO RELATED APPLICATION

This application is a division of application Ser. No. 386,854 filed Aug. 9, 1973.

This invention relates to cyclic N-substituted derivatives of 1,4-benzene disulphonamide which have cerebral vasodilator activity and are therefore useful for treating conditions attributable to a restriction of blood flow to the brain. Such conditions include atherosclerosis, occlusion of blood vessels in the brain, stroke and other cerebrovascular diseases. Particularly useful compounds according to this aspect of the invention are those which have a selective effect on the cerebral vasculature, with a comparatively small effect on blood vessels in other tissues such as peripheral tissue and the kidneys, and so do not cause a serious fall in blood pressure or increase in diuresis.

The aforesaid derivatives include compounds of the formula

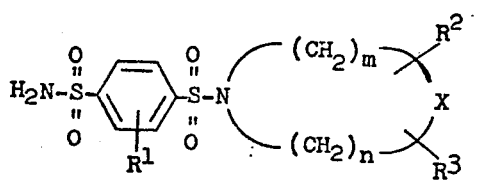

those of the formula

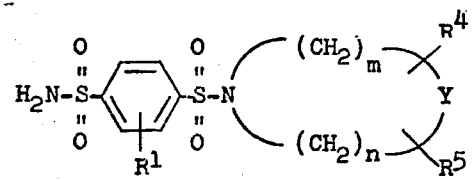

and the salts thereof with pharmaceutically acceptable cations wherein $R^1$ is 3-trifluoromethyl, chloro, bromo or fluoro; n and m are each two or three; X is oxygen or sulphur; $R^2$ and $R^3$, when taken separately, are each hydrogen or alkyl having 1 to 4 carbon atoms; $R^2$ and $R^3$, when taken together, are alkylene having 2 to 4 carbon atoms; Y is methylene or a single bond; $R^4$ and $R^{5}$ when taken separately, are each hydrogen, hydroxy or alkoxy having 1 to 4 carbon atoms and $R^4$ and $R^{5}$ when taken together, are oxo or alkylene dioxy having 2 to 4 carbon atoms, each oxygen atom in $R^4$ and $R^5$, when taken separately, and in $R^4$ and $R^5$, when taken together, being separated from the nitrogen atom of the heterocyclic ring by two or more carbon atoms.

Certain of the aforesaid compounds are old in the art as shown in U.S. Pat. No. 3,165,550. Those of the aforesaid compounds of the present invention which are unobvious include compounds of formula (I) and formula (II) and the salts thereof with pharmaceutically acceptable cations wherein $R^1$ is 3-trifluoromethyl, chloro, bromo or fluoro; n and m are each 2 or 3; X is oxygen; $R^2$ and $R^3$, when taken separately, are each alkyl having 1 to 4 carbon atoms; $R^2$ and $R^3$, when taken together, are alkylene having 2 to 4 carbon atoms; Y is methylene; $R^4$, when taken separately, is hydroxy or alkoxy having 1 to 4 carbon atoms; $R^5$, when taken separately, is hydrogen, hydroxy or alkoxy having 1 to 4 carbon atoms and $R^4$ and $R^5$, when taken together, are oxo or alkylene dioxy having 2 to 4 carbon atoms, each oxygen atom in $R^4$ and $R^5$, when taken separately, and in $R^4$ and $R^5$, when taken together, being separated from the nitrogen atom of the heterocyclic ring by two or more carbon atoms.

Preferred compounds of the invention having cerebral vasodilator activity are those of formula (I) in which X is an oxygen atom. Another preferred group are those compounds of formula (II) in which Y is a methylene group and $R^4$ and $R^5$ together represent an oxo group or an alkylene dioxy group having 1 to 4 carbon atoms, each of these being attached to the methylene group, i.e., to Y. Another preferred group of compounds are those of formula (II) wherein Y is methylene, $R^4$ is hydroxy or alkoxy having 1 to 4 carbon atoms and $R^5$ is hydrogen. Of those preferred compounds of formula (I) in which X is an oxygen atom, particularly preferred are those in which $R^2$ and $R^3$ are each alkyl having 1 to 4 carbon atoms. Of those preferred compounds in which Y is a methylene group or an oxygen atom, particularly preferred are those in which n and m are each 2, i.e., the heterocyclic ring is a 4-piperidone ring or a dialkyl or alkylene ketal thereof, or a morpholine ring.

Also particularly preferred for their cerebral vasodilator activity are compounds of the invention having one or more of the preferred structural characteristics just mentioned wherein $R^1$ is 2-chloro, 2-bromo or 3-trifluoromethyl.

The compounds of this invention, other than those in which $R^4$ and $R^5$ together are an oxo group, may be prepared from 4-sulphamoyl-benzene sulphonyl chlorides of the formula:

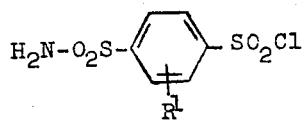

by reaction with a cyclic amine of the formula:

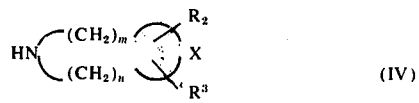

or with a cyclic amine of the formula:

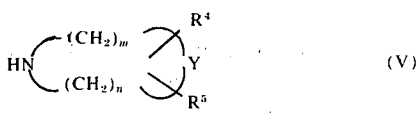

in a suitable solvent, e.g., acetone or dichloromethane. Preferably, the reaction is carried out in the presence of an excess of the amine reactant or in the presence of an equivalent amount of an organic tertiary amine to remove the hydrochloric acid formed in the reaction. The reaction is completed in from 1 to 24 hours at 20°C. or may be carried out at elevated temperatures, i.e., 30 to 100°C. for periods of from 1 to 8 hours. The product may be isolated by simply adding the reaction mixture to normal aqueous hydrochloric acid solution, filtering, washing and recrystallizing from a suitable solvent.

Compounds of the invention in which $R^1$ consists of chloro, bromo, fluoro or trifluoromethyl, in positions meta to the unsubstituted sulphamoyl group, may also be prepared from the appropriately substituted 4-nitrobenzene sulphonyl chloride by reaction first with the cyclic amine of formula (IV) or (V) to form a compound of the formula:

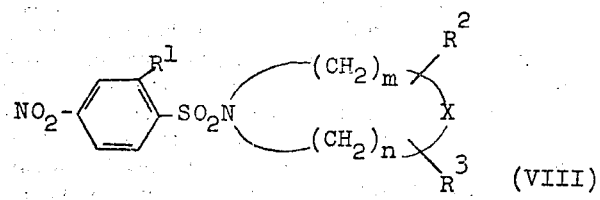

or of the formula:

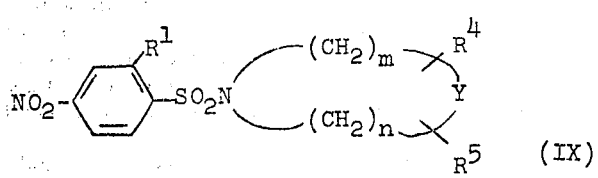

wherein $R^1$ is a chlorine, bromine or fluorine atom or a trifluoromethyl group and $R^4$ and $R^5$, together, are not an oxo group, and the compound of formula (VIII) or (IX) is then reduced to the corresponding amino compound and the latter is converted to the corresponding sulphamoyl compound by diazotization, treatment with sulphur dioxide in the presence of a cupric salt and then with ammonia.

Finally compounds in which $R^4$ and $R^5$ together are an oxo group are prepared from the corresponding dialkyl or alkylene ketals, i.e., compounds of formula (II) in which $R^4$ and $R^5$ are two alkoxy groups or an alkylene dioxy group attached to a single carbon atom, by methods well known in the art, e.g., by treatment with concentrated hydrochloric acid in aqueous dimethylformamide.

The salts of the present invention include those based on any pharmaceutically acceptable cation. The preferred pharmaceutically acceptable cations are those of the alkali metals, particularly sodium and potassium. Said salts are easily obtained in accordance with conventional methods. For example, the selected compound of formula (I) or formula (II) is dissolved in an aqueous or alcoholic solution of an alkali metal hydroxide such as sodium or potassium hydroxide and the resulting solution is simply concentrated.

In accordance with the treatment method of the present invention the herein described compounds can be administered to an affected subject via the oral or parenteral route. Generally, there is a significant effect in increasing cerebral blood flow in cats, dogs and baboons at dose levels of from 2.5 to 25 mg/kg intravenously or from 10 to 50 mg/kg orally when administered three times a day, the effect being cumulative. Although the physician will determine the precise dosage for a human patient, it generally will range from 0.5 to 100 mg/kg for intravenous administration and from 2 to 200 mg/kg for oral administration, each dosage form being administered four times a day.

The compounds of the invention may be administered alone, but will generally be administered in admixture with a pharmaceutical carrier selected with regard to the intended route of administration and standard pharmaceutical practice.

For administration orally in the form of tablets, or capsules, it has been found advantageous to dissolve or disperse the compound in finely divided form (e.g. 30 microns or less in dimensions) in a matrix of a high molecular weight solid polyethylene glycol, e.g. a polyethylene glycol of average molecular weight 6,000 to 7,500 such as "Carbowax" 6,000. A non-ionic wetting agent as dispersion aid, e.g. a polyoxyethylene monostearate of average molecular weight about 1,000 such as "Myrj" 52, is preferably also included. For this type of formulation, the compound together with the dispersion aid may be dissolved in the molten polyethylene glycol and cooled, or alternatively may be mixed as an aqueous dispersion with the polyethylene glycol to form a paste and dried, and then, together with other excipients if desired, either granulated prior to compression into tablets or filled directly into capsules, by techniques well known in the art.

Alternatively, tablets may be formed in which a major part of the excipient is composed of a material which, when compressed, has a slower rate of dissolution than that normally achieved by standard tableting practice. Such materials include sugars and edible aminoacids such as glycine. The compound (in finely divided form) is preferably first mixed with the said material and then granulated with a comparatively small amount of the high molecular weight polyethylene glycol and a dispersion aid, before forming into tablets in the usual way.

For parenteral administration, the compounds, being acidic, are best used in the form of sterile aqueous solutions of their alkali metal (e.g. sodium) salts aand such solutions may contain other solutes (e.g. sodium chloride) to ensure the stability of the solutions and their compatibility with body fluids, e.g. blood, when the compound is to be administered intravenously, intramuscularly or subcutaneously. The alkali metal salt solution may conveniently be formed by dissolving the compound (and any other solute required) in the sterile water and adjusting the pH to a value in the range from 10.5 to 12.0 with the appropriate alkali metal hydroxide.

The following examples illustrate preparation of the cerebral vasodilators of this invention.

EXAMPLE I

2-Chloro-4-(4-methoxypiperidinosulphonyl)benzene sulphonamide

Triethylamine (4.2 ml) and 4-methoxypiperidine (3.15 g) were added to a solution of 3-chloro-4-sulphamoyl-benzene sulphonyl chloride (8.7 g) in acetone (100 ml). The mixture was stirred at room temperature for 1 hour and then poured into 50 ml of N-hydrochloric acid. The resulting product was removed by filtration, washed with water and recrystallized from isopropanol to give the desired compound (8.4 g), m.p. 165°–167°C.

Analysis:
Found: C, 39.16; H, 4.91; N, 7.53%.
Calculated for $C_{12}H_{17}ClN_2O_5S_2$: C, 39.06; H, 4.64; N, 7.59%.

EXAMPLES II to XXII

The compounds shown in Table I were prepared by the method of Example I, using the appropriate cyclic amine and substituted 4-sulphamoyl-benzene sulphonyl chloride as starting material. The $R^1$-substituted 4-sulphamoyl-benzene sulphonyl chloride starting materials for these Example, as well as for Example I, are either known compounds, disclosed in U.S. Pat. No. 3,165,550, or are readily prepared by the methods described therein, from the corresponding $R^1$-substituted 4-aminobenzene sulphonamides.

The compounds of Table I are represented by the formula:

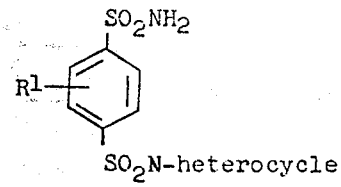

TABLE I

| Example | $R^1$ | N-heterocycle | m.p.°C. | Analysis % (theoretical in brackets) C | H | N |
|---|---|---|---|---|---|---|
| II | 3-Cl | -N⟨⟩-OCH₃ | 122–123 | 39.08 (39.06 | 4.81 4.64 | 7.96 7.59) |
| III | 2-Cl | -N⟨⟩-OH | 230–234 | 37.50 (37.23 | 4.26 4.26 | 8.12 7.90) |
| IV | 2-Cl | -N⟨⟩ | 175–177 | 40.93 (40.84 | 5.09 4.86 | 7.84 7.94) |
| V | 2-Cl | -N⟨O⟩ | 187–188 | 35.48 (35.25 | 3.84 3.82 | 8.58 8.22) |
| VI | 2-Cl | -N⟨⟩ OCH₃ | 151–152 | 39.19 (39.06 | 4.76 4.64 | 7.84 7.59) |
| VIII | 2-Cl | -N⟨CH₃,O,CH₃⟩ | 198–199 | 38.95 (39.09 | 4.62 4.64 | 7.96 7.59) |
| IX | 3-Cl | -N⟨O⟩ | 95–98 | 34.97 (35.25 | 4.15 3.82 | 8.38 8.22) |
| X | 2-F | -N⟨⟩-OCH₃ | 199–200 | 41.00 (40.90 | 4.87 4.86 | 7.80 7.95) |
| XI | 2-Cl | -N⟨⟩⟨OCH₂,OCH₂⟩ | 172 | 39.52 (39.34 | 4.31 4.31 | 7.15 7.06) |

TABLE I-continued
| Example | R¹ | N-heterocycle | m.p.°C. | Analysis % (theoretical in brackets) C | H | N |
|---|---|---|---|---|---|---|
| XIII | 2-Cl |  | 130–132 | 37.42 (37.23 | 4.43 4.26 | 8.33 7.90) |
| XIV | 2-F | 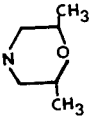 | 176–178 | 41.02 (40.89 | 4.93 4.86 | 7.95 7.95) |
| XV | 2-Cl |  | 193–195 | 39.4 (40.0 | 4.3 4.45 | 8.8 8.3) |
| XVI | 2-Br |  | 161–163 | 34.86 (34.93 | 4.14 4.15 | 6.71 6.79) |
| XVIII | 2-Cl |  | 179–180 | 33.74 (33.67 | 3.73 3.64 | 7.54 7.85) |
| XVIII | 2-Cl |  | 159–162 | 37.58 (37.23 | 4.31 4.26 | 7.82 7.89) |
| XIX | 2-Cl |  | 169–173 | 39.37 (39.07 | 4.69 4.65 | 7.40 7.59) |
| XX | 2-Cl | 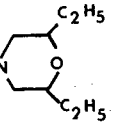 | 123–125 | 42.78 (42.36 | 5.51 5.33 | 6.85 7.06) |
| XXI | 2-Cl |  | 176–178 | 39.09 (39.29 | 4.14 4.09 | 7.71 7.64) |
| XXII | 2-Br | 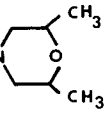 | 200–202 | 34.91 (34.94 | 4.10 4.15 | 7.07 6.79) |
| XII | 2-Cl | 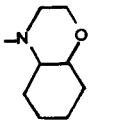 | 198–200 | 43.01 (42.58 | 5.24 4.85 | 7.34 7.10) |
| VII | 2-Br | 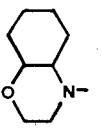 | 215–216 | 38.35 (38.26 | 4.36 4.36 | 6.32 6.38) |

EXAMPLE XXIII

2-Chloro-4-(4-oxopiperidinosulphonyl)-benzene sulphonamide

A solution of the product of Example XI (1.2 g) in 30% aqueous dimethylformamide (50 ml) and concentrated hydrochloric acid (1.5 ml) was stirred under reflux for 1 hour. The mixture was evaporated to small volume and the resulting precipitate was filtered off and recrystallized from an acetonehexane mixture to give the desired product (500 mg), m.p. 195°–196°C.

Analysis:
Found: C, 37.33; H, 3.82; N, 7.96%.
Calculated for $C_{11}H_{13}ClN_2O_5S_2$: C, 37.50; H, 3.69; N, 7.62%.

EXAMPLE XXIV

3-Trifluoromethyl-4-(4-methoxypiperidinosulphonyl)-benzene sulphonamide

A. Triethylamine (1.0 g) and 4-methoxypiperidine (1.15 g) were added to a solution of 4-nitro-2-trifluoromethylbenzene sulphonyl chloride (2.89 g) in methylene chloride (40 ml). The mixture was stirred at 25°C. for 2 hours and then evaporated to dryness in vacuo. The residual oil was triturated with 1:1 aqueous isopropanol and the resulting solid was recrystallized from isopropanol to give 1-(4-methoxypiperidinosulphonyl)-4-nitro-2-trifluoromethyl-benzene, m.p. 141°–143°C.

B. The product of (A) (13.5 g) as dissolved in methanol (200 ml) and hydrogenated at 50 p.s.i. and 50°C. in the presence of 5% palladium-on-charcoal (1.0 g) to yield 4-(4-methoxypiperidinosulphonyl)-3-trifluoromethyl-aniline (8.9 g), m.p. 145°–147°C., recrystallized from isopropanol.

C. A solution of the diazonium chloride of the product of (B), prepared by the addition of a solution of sodium nitrite (1.73 g) in water (15 ml) to the product of (B) (8.4 g) in concentrated hydrochloric acid (60 ml), was added at 25°C. to a suspension of cupric chloride dihydrate (2.2 g) in acetic acid (80 ml) previously saturated with sulphur dioxide. The mixture was stirred for 1 hour and the resulting precipitate was filtered, washed with water, dried and recrystallized from an acetone-hexane mixture to give 4-(4-methoxypiperidinosulphonyl)-3-trifluoromethyl-benzene sulphonyl chloride (5 g), m.p. 117°–119°C.

D. The product of (C) (4.5 g) was added to concentrated ammonium hydroxide (80 ml) and the mixture was heated at 60°C for 1 hour. The resulting solution was cooled, treated with excess 2N hydrochloric acid and the precipitate thus obtained was filtered, washed with water, dried and recrystallized from isopropanol to give the required product (2.3 g), m.p. 136°–137°C.

Analysis:
Found: C, 38.74; H, 4.22; N, 6.62%.
Calculated for $C_{13}H_{17}F_3N_2O_5S_2$: C, 38.81; H, 4.26; N, 6.97%.

The activity of compounds of the invention as cerebral vasodilators is determined by the following method. Cats are anaesthetised with chloralose (80 mg/kg, intravenously) after induction with halothane, nitrous oxide/oxygen (3:1 v/v). The animals are allowed to breathe normal room air and the rate and depth of respiration, heart rate and femoral arterial pressure are recorded. Electromagnetic flow probes are placed around the ipsilateral vertebral artery. Zero flow is established by momentarily occluding the arteries in order to calibrate the flow probes. The test compound (dissolved in N/10 sodium hydroxide in isotonic saline with warming and mixing and then back titration to pH 10 with dilute hydrochloric acid) is given at 10 or 25 mg/kg via a femoral vein and readings are taken at intervals for up to 2 hours. Control observations after administration of the saline vehicle alone are also made. The criterion for selecting the preferred compounds is on the basis of increases in ipsilateral vertebral arterial flow at 10 mg/kg which are sustained over a period of 30 minutes as shown in Table II. Blood flow is assessed by measuring the peak (systolic) pulsatile flow and the mean pulsatile flow. The products of Examples VIII, XXII, III and V have been found to give significant increases in peak and mean pulsatile flow at 10 mg/kg. The product of Example VIII is outstanding at that dosage. Table II hereinafter summarizes results obtained with representative cerebral vasodilators of the present invention in accordance with this method.

The effect of compounds of the invention on blood pressure and diuresis is determined in dogs by standard methods. Several compounds have been found to be particularly advantageous in having very little hypotensive or diuretic activity, including the products of Examples I and XXII.

TABLE II

| Compound of Example | Dose (mg/kg) | Activity Data[1] IVF:% | t | Side Effects |
|---|---|---|---|---|
| I | 10 | 42 | 40–50 | — |
| II | 10 | 10 | 5–10 | — |
|  | 25 | (200) | 20–30 | fasciculation at 20 min. |
| V | 10 | 40 | 30–60 | — |
| VIII | 10 | 82 | 60–120 | — |
| X | 25 | 40 | 40–60 | — |
| XI | 10 | 13 | 5–8 | — |
| XXII | 10 | 30 | 40–50 | — |
|  | 25 | 33 | 20–30 | — |
| XXIV | 10 | 20 | 5–10 | — |
|  | 25 | 70 | 20–40 | — |
| III | 10 | 34 | 40–60 | — |

[1]mean maximum increase in blood flow (%) and duration of action in minutes (t).
IVF = ipsilateral vertebral artial flow.

EXAMPLE XXV

Tablet formulation

|  | mg/tablet |
|---|---|
| Active ingredient[1] | 100.0 |
| glycine | 320.7 |
| PEG 6000[2] | 40.0 |
| Myrj 52[3] | 20.0 |
| magnesium stearate | 4.9 |
| gelatin | 2.4 |
|  | 488.0 |

[1]mean particle diameter (from surface area/g) less than 16 microns.
[2]polyoxyethylene glycol of mean molecular weight 6000.
[3]a foodstuffs quality surfactant: polyoxyethylene stearate.

The active compound and glycine are granulated with an aqueous solution of the PEG 6000, Myrj 52 and gelatin, prior to adding the magnesium stearate and tableting in the usual way.

EXAMPLE XXVI

| Capsule formulation | mg/capsule |
|---|---|
| Active ingredient[1] | 100.0 |
| PEG 6000[2] | 280.0 |
| Myrj 52[3] | 20.0 |
| | 400.0 |

[1] mean particle diameter less than 3 microns.
[2] and (3) as in Example XXV

The active compound is ball-milled in water to achieve the small particle size, mixed with the PEG 6000 and Myrj 52 as a paste and then dried at 40°C. to form a powder which is then filled into capsules in the usual way.

EXAMPLE XXVII

| Parenteral formulation | mg/ml |
|---|---|
| Active ingredient | 7.5 |
| sodium chloride | 7.9 |
| sodium hydroxide | (sufficient in pH adjustment) |
| water | (sufficient to make up volume) |

The active ingredient and sodium chloride are dissolved in sterile, pyrogen-free and carbon dioxide-free water under nitrogen, the pH is adjusted to 11.75 with 10% aqueous sodium hydroxide and the volume made up with similar water. The solution is then filled into 5 or 10 ml. ampoules through a filter and autoclaved at 115°C. for 30 minutes.

What is claimed is:

1. A process for increasing cerebral blood flow in a subject which comprises administering to said subject a cerebral blood flow increasing amount of a compound selected from the group consisting of:

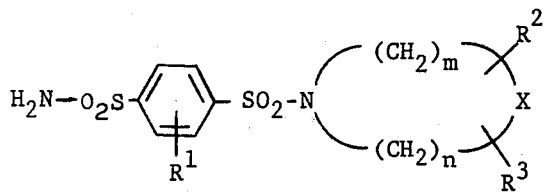

and their salts with pharmaceutically acceptable cations wherein $R^1$ and 3-trifluoromethyl, chloro, bromo or fluoro; $n$ and $m$ are each two or three; X is oxygen or sulfur; $R^2$ and $R^3$, when taken separately, are each hydrogen or alkyl having 1 to 4 carbon atoms and $R^2$ and $R^3$, when taken together, are alkylene having 2 to 4 carbon atoms.

2. The process of claim 1 wherein X is oxygen.
3. The process of claim 2 wherein each of $R^2$ and $R^3$ is alkyl having 1 to 4 carbon atoms.
4. The process of claim 3 wherein $R^1$ is chloro.
5. The process of claim 1 wherein $R^1$ is 2-chloro, $m$ and $n$ are each 2, X is oxygen, $R^2$ is 2-methyl and $R^3$ is 6-methyl.

* * * * *